ns Patent [19]

von Daehne et al.

[11] 4,119,717
[45] Oct. 10, 1978

[54] 16-S-ACYL DERIVATIVES OF FUSIDIC ACID

[75] Inventors: Welf von Daehne, Rungsted Kyst; Poul Rødbroe, Rasmussen, Frederikssund, both of Denmark

[73] Assignee: Leo Pharmaceutical Products Ltd. A/S Lovens Kemiske Fabrik Produktionsaktieselskab, Ballerup, Denmark

[21] Appl. No.: 806,376

[22] Filed: Jun. 14, 1977

[30] Foreign Application Priority Data

Jul. 5, 1976 [GB] United Kingdom ............... 27921/76

[51] Int. Cl.² ........................................... A61K 31/56
[52] U.S. Cl. .................................... 424/238; 424/239; 424/240; 260/397.1
[58] Field of Search ..................... 260/397.1; 424/238, 424/239, 240

[56] References Cited

U.S. PATENT DOCUMENTS 4,004,004  1/1977  Von Daehne ..................... 260/397.1
4,060,606  11/1977  Von Daehne et al. ........... 260/397.1

Primary Examiner—Elbert L. Roberts
Attorney, Agent, or Firm—Cushman, Darby & Cushman

[57] ABSTRACT

The present invention relates to a new series of fusidic acid derivatives, to salts and easily hydrolysable esters thereof, to the preparation of these compounds, and to pharmaceutical compositions containing the compounds, the new fusidic acid derivatives having the general formula:

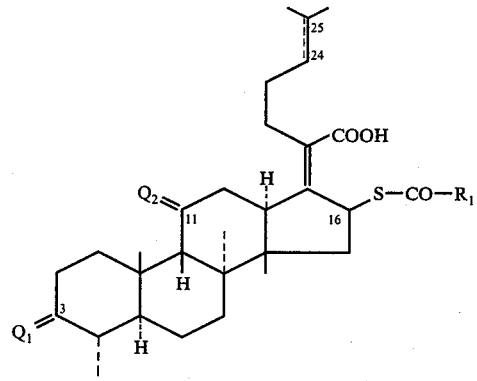

in which the dotted line between C-24 and C-25 indicates that the carbon atoms in question are connected by either a double bond or a single bond, and in which $Q_1$ represents oxygen or one of the groupings

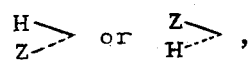

Z being a hydroxy group, a halogen atom, an alkylsulfonyloxy or arylsulfonyloxy group, such as methanesulfonyloxy or p-toluenesulfonyloxy, an azido or a nitro group, $Q_2$ is oxygen or the grouping

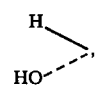

and $R_1$ stands for a straight or branched alkyl radical having from 1 to 6 carbon atoms, such as methyl, ethyl, propyl, isopropyl, butyl, isobutyl, tert-butyl or the known isomers of pentyl and hexyl, a phenyl or a heterocyclyl radical having 5 to 6 ring atoms and containing nitrogen, oxygen and/or sulfur atoms, these radicals being optionally substituted with halogen, nitro, lower alkyl or lower alkoxy radicals.

The present compounds show both in vitro and in vivo interesting antimicrobial and pharmacokinetic properties.

30 Claims, No Drawings

16-S-ACYL DERIVATIVES OF FUSIDIC ACID

The present invention relates to a new series of fusidic acid derivatives, to salts and easily hydrolysable esters thereof, to the preparation of these compounds, and to pharmaceutical compositions containing the compounds. The new compounds have the general formula:

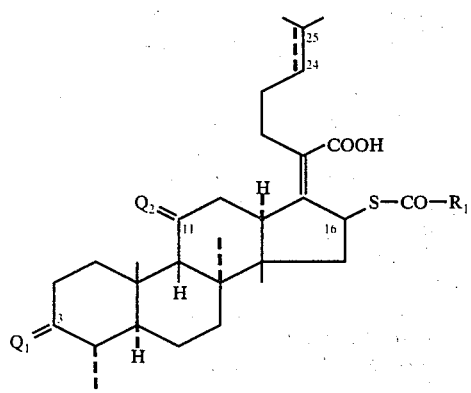

I in which $Q_1$ represents oxygen or one of the groupings

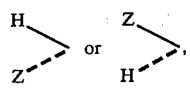

Z being a hydroxy group, a halogen atom, an alkylsulfonyloxy or arylsulfonyloxy group, such as methanesulfonyloxy or p-toluenesulfonyloxy, an azido or a nitro group, $Q_2$ is oxygen or the grouping

and $R_1$ stands for a straight or branched alkyl radical having from 1 to 6 carbon atoms, such as methyl, ethyl, propyl, isopropyl, butyl, isobutyl, tert-butyl or the known isomers of pentyl and hexyl, a phenyl or a heterocyclyl radical having 5 or 6 ring atoms and containing nitrogen, oxygen and/or sulfur atoms, these radicals being optionally substituted with halogen, nitro, lower alkyl or lower alkoxy radicals.

In formula I the dotted line between C-24 and C-25 indicates that the carbon atoms in question are connected by either a double bond or a single bond.

Where not otherwise stated the term "lower" indicates a carbon atom content of 1 to 4.

The compounds of the invention can be used as such or in the form of salts or easily hydrolysable esters. The salts of the compounds are especially the pharmaceutically acceptable, non-toxic salts, such as alkali metal salts and alkaline earth metal salts, e.g. sodium, potassium, magnesium or calcium salts, as well as salts with ammonia or suitable non-toxic amines; for certain purposes also the silver salts of the compounds may be used, especially for topical treatment.

The easily hydrolyzable esters can e.g. be alkanoyloxyalkyl, aralkanoyloxyalkyl, aroyloxyalkyl esters, such as acetoxymethyl, pivaloyloxymethyl, benzoyloxymethyl esters, and the corresponding 1'-oxyethyl derivatives, or alkoxycarbonyloxyalkyl esters, such as methoxycarbonyloxymethyl, ethoxycarbonyloxymethyl esters, and the corresponding 1'-oxyethyl derivatives, or lactonyl esters, such as phthalidyl esters, or dialkylaminoalkyl esters, such as diethylaminoethyl esters.

The antibacterial properties of fusidic acid are well known, and also that variations in the structure may cause a considerable or even complete loss of such activity.

Now, however, it has been found, that the compounds of the present invention both in vitro and in vivo show interesting antimicrobial and pharmacokinetic properties. Thereby the compounds of the invention can be used in the treatment of bacterial infections in humans and animals. In vitro investigations have for instance shown that the compounds are more potent than fusidic acid against a number of bacteria, e.g. staphylococci, streptococci, corynebacteriae, neisseriae, clostridiae and bacteroides species, and *Bacillus subtilis*, as can be seen from the following table:

| | Antibacterial activity of compounds of formula I | | | | | | | |
|---|---|---|---|---|---|---|---|---|
| | | | | | Concentration required for 50% inhibition (μg/ml) | | | |
| | Substituents | | | C-24,24 | Staph.aureus | Staph.aureus | Strep.pyogenes | Strep.sp. | Bacteroides fragilis |
| Example | $Q_1$ | $Q_2$ | $R_1$ | bond | Leo CC 178 B | Leo CC 178 A | Leo EC | Leo EG 2 | Leo JA 2 |
| 1 | H,α-OH | H,α-OH | $CH_3$ | double | 0.010 | 6.3 | 0.20 | 0.20 | 0.79 |
| 3 | H,α-OH | H,α-OH | $CH_3$ | single | 0.008 | 3.2 | 0.16 | 0.25 | 0.50 |
| 4 | H,α-OH | H,α-OH | $C_6H_5$ | single | 0.50 | 1.6 | 0.20 | 0.63 | 1.6 |
| 7 | H,α-OH | O | $CH_3$ | double | 0.020 | 20 | 1.0 | 2.0 | 2.0 |
| 8 | H,α-OH | O | $CH_3$ | single | 0.020 | 16 | 1.0 | 2.0 | 2.0 |
| 21 | H,β-Br | H,α-OH | $CH_3$ | double | 0.13 | 4.0 | 0.32 | 1.0 | 3.2 |
| 22 | H,β-Br | H,°-OH | $CH_3$ | single | 0.079 | 1.6 | 0.79 | 1.6 | 2.0 |
| 29 | H,β-Cl | H,α-OH | $CH_3$ | double | 0.50 | 2.0 | 0.63 | 1.6 | 1.3 |
| 28 | H,β-$N_3$ | H,α-OH | $CH_3$ | single | 1.6 | 2.0 | 0.63 | 0.63 | 1.6 |
| 36 | H,°-$N_3$ | H,α-OH | $CH_3$ | single | 0.063 | 5.0 | 0.40 | 2.0 | 5.0 |
| | Fusidic acid | | | | 0.025 | 16 | 0.63 | 1.6 | 1.6 |

In vivo investigations in rats, dogs, and human volunteers have shown that the compounds of the invention are absorbed efficiently from the gastro-intestinal tract and are practically non-toxic.

The compounds of formula I can be prepared by a method comprising reacting a compound of the general formula II with a compound of the general formula III to form, with inversion of configuration at C-16, a compound of the general formula IV:

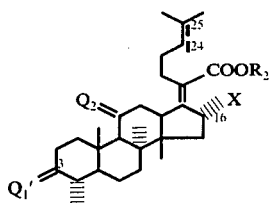

II

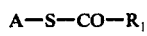

III

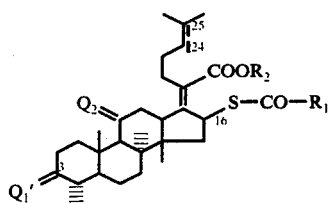

in which formulae $Q_1'$ stands for oxygen or one of the groupings

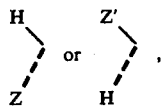

Z' being a hydroxy or formyloxy group, an alkylsulfonyloxy or arylsulfonyloxy group, e.g. methanesulfonyloxy or p-toluenesulfonyloxy, or a chlorine, bromine or iodine atom, $Q_2$, $R_1$ and the dotted line between C-24 and C-25 have the meaning as defined above, A stands for hydrogen or a cation, such as $Na^+$, $K^+$, $Ag^+$, an ammonium, or trialkylammonium ion, X is a chlorine, bromine or iodine atom, and $R_2$ represents an alkanoyloxyalkyl or aroyloxyalkyl radical, e.g. acetoxymethyl, pivaloyloxymethyl or benzoyloxymethyl, a benzyl radical or a substituted benzyl radical, e.g. p-nitrobenzyl or p-methoxybenzyl.

The reactions are performed in an inert organic solvent, e.g. dimethylformamide, and at temperatures between 0° C. and 40° C., preferably at room temperature.

The preparation of the starting compounds of formula II is described in our co-pending British Complete Specification of Application No. 26989/75[+)] or can be performed by analogous methods.

The compounds of formula IV in which $Q_1'$ stands for the groupings

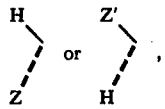

Z' being an alkylsulfonyloxy or arylsulfonyloxy group, or a chlorine, bromine or iodine atom, can be converted, with inversion of configuration at C-3, into corresponding compounds of formula IV in which Z' stands for a halogen atom, an azido or a nitro group by reaction with nucleophilic agents such as alkalimetal iodides, azides or nitrites, tetrabutylammonium chloride, bromide or iodide, or silver fluoride.

These conversions are performed in reaction-inert organic solvents, e.g. dimethylformamide, acetone or acetonitrile, and at temperatures between 0° C. and 80° C.

Compounds of formula IV in which $Q_1'$ stands for oxygen or one of the groupings $$\underset{Z}{\overset{H}{\diagdown}}\diagup\quad \text{or} \quad \underset{H}{\overset{Z}{\diagdown}}\diagup,$$

Z having the above meaning, and $R_2$ represents an easily hydrolyzable ester radical as defined above are easily hydrolyzable esters of the corresponding acids of formula I and therefore part of the invention.

The compounds of formula IV are converted into the compounds of formula I by different procedures depending on what $R_2$ stands for. Mild hydrolysis in the presence of an inorganic or organic acid, e.g. hydrochloric or p-toluenesulfonic acid, in aqueous methanol or ethanol, or alcoholysis in the presence of a weak base, e.g. sodium or potassium carbonate, will be preferred if $R_2$ represents an alkanoyloxyalkyl or aroyloxyalkyl radical, and catalytic hydrogenation using e.g. palladium on carbon as a catalyst is preferred in the case where $R_2$ stands for a benzyl radical or a substituted benzyl radical.

Compounds of the general formula I in which $Q_1$ and/or $Q_2$ stand for oxygen can also be prepared from the corresponding compounds of formula I in which $Q_1$ and/or $Q_2$ stand for the grouping $$\underset{HO}{\overset{H}{\diagdown}}\diagup$$

by oxidation methods known to a man skilled in the art.

The compounds of formula I in which $Q_1$ contains a halogen atom, an azido or a nitro group, as defined above, can also be prepared directly from the compounds of formula I in which $Q_1$ stands for $$\underset{Z''}{\overset{H}{\diagdown}}\diagup\quad \text{or} \quad \underset{H}{\overset{Z''}{\diagdown}}\diagup,$$

Z" being a hydroxy, alkyl- or arylsulfonyloxy group, or from easily hydrolyzable esters thereof by well known processes, e.g. conversion with inversion of configuration at C-3 of a hydroxy group into halogen, or nucleophilic substitution of an alkyl- or arylsulfonyloxy group with silver fluoride, a tetrabutylammonium halogenide or an alkalimetal azide or nitrite.

The salts and the easily hydrolysable esters of the compounds of formula I can be prepared in known manner by methods described in the literature.

Compounds of the invention in which there are single bonds between C-24 and C-25 can also be prepared from the corresponding unsaturated analogues by reduction, e.g. a catalytic hydrogenation using for instance palladium on carbon as a catalyst.

It is a further object of the present invention to provide pharmaceutical compositions which are useful in the treatment of infectious diseases in the human and veterinary practice.

With this object in view, the compositions of the invention contain as an active component at least one

[+)] corresponding to German Offenlegungsschrift No. P 26 28 360 member selected from the group consisting of compounds of the formula I, salts thereof with non-toxic, pharmaceutically acceptable bases, and easily hydrolyzable esters together with solid or liquid pharmaceutical carriers and/or diluents.

In the said compositions, the proportion of therapeutically active material to carrier substance can vary between 1% and 95% by weight. The compositions can be worked up to various pharmaceutical forms of presentation, such as granulate, tablets, pills, dragees, suppositories, capsules, sustained-release tablets, suspensions, ointments, creams, injection medicine, or so far as mixtures are concerned, they may be filled in bottles or tubes or similar containers. Pharmaceutical organic or inorganic, solid or liquid carriers and/or diluents suitable for oral, enteral, parenteral or topical administration can be used to make up compositions containing the present compounds. Water, gelatine, lactose, starch, magnesium stearate, talc, vegetable and animal oils and fats, benzyl alcohol, gum, polyalkylene glycol, petroleum jelly, cocoa butter, lanolin or other known carriers for medicaments are all suitable, while stabilizing agents, wetting and emulsifying agents, salts for varying the osmotic pressure or buffers for securing an adequate pH-value of the composition can be used as auxiliary agents.

Furthermore, the composition may contain other pharmaceutically active components which can appropriately be administered together with the compounds of the invention in the treatment of infectious diseases, such as other suitable antibiotics, in particular such antibiotics, which may enhance the activity and/or prevent development of resistance. Such antibiotics include penicillins, cephalosporins, tetracyclines, rifamycins, erythromycin, lincomycin, clindamycin, fusidic acid, and other fusidic acid derivatives, e.g. those described in our co-pending British Complete Specification of Patent Application No. 26989/75[+)] and our co-pending British Complete Specification of Patent Application No. 49714/75[++)]. Other compounds which advantageously may be combined with the compounds of the inventions, especially in topical preparations, include e.g. corticosteroids, like hydrocortisone, triamcinolone or fluocinolone.

For granulates, tablets, capsules or dragees, the pharmaceutical composition of the invention appropriately contains from 25 percent to 98 percent of the active substance of the invention, and in oral suspensions the corresponding amount is appropriately from 2–25 percent.

For parenteral use the compounds are preferably given by intravenous infusion of an aqueous solution containing from 0.1 to 2 percent of the active ingredient, or the compound might be given by injection of the compounds in pharmaceutical compositions with from 1 to 20 percent active ingredient.

When the compounds are administered in the form of salts with pharmaceutically acceptable non-toxic bases, the preferred salts are for instance the easily water-soluble sodium, potassium or diethanolamine salts, but other pharmaceutically acceptable and non-toxic salts may be used, for instance salts which are slightly soluble in water, in order to obtain a particular and appropriate rate of absorption.

As indicated above, the present compounds may be worked up to pharmaceutical forms of presentation including suspensions, ointments and creams. A pharmaceutical preparation for oral treatment may also be in the form of a suspension of a compound of formula I as such or in the form of a sparingly soluble salt with a pharmaceutically acceptable base or an easily hydrolyzable ester, the preparation containing from 20 to 100 mg per ml of vehicle.

A pharmaceutical preparation for topical treatment may be in the form of an ointment or cream containing a compound of formula I or a salt thereof in an amount of from 0.5 to 10 g per 100 g of preparation.

Another object of the invention resides in the selection of a dose of the compounds of the invention which dose can be administered so that the desired activity is achieved without simultaneous secondary effects. In the human systemic therapy, the compounds and their salts and easily hydrolyzable esters are conveniently administered (to adults) in dosage units containing not less than 50 mg and up to 1000 mg, preferably from 200 to 750 mg, calculated as the compound of formula I.

By the term "dosage unit" is meant a unitary, i.e. a single dose which is capable of being administered to a patient, and which may be readily handled and packed, remaining as a physically stable unit dose comprising either the active material as such or a mixture of it with solid or liquid pharmaceutical diluents or carriers.

In the form of a dosage unit, the compound may be administered once or more times a day at appropriate intervals, always depending, however, on the condition of the patient, and in accordance with the prescription made by the medical practitioner.

Thus in systemic treatment a daily dose will preferably be an amount of from 0.5 to 3 g of a compound of the invention.

By the term "dosage unit" is in connection with the topical use meant a unitary, i.e. a single dose capable of being administered topically to the patients and applicating per sq. centimeter of the infected area from 0.1 mg to 10 mg and preferably from 0.2 mg to 1 mg of the compound in question.

If the composition is to be injected, a sealed ampoule, a vial or a similar container may be provided containing a parenterally acceptable aqueous or oily injectable solution or dispersion of the active material as the dosage unit.

The parenteral preparations are in particular useful in the treatment of conditions in which a quick response to the treatment is desirable. In the continuous therapy of patients suffering from infectious diseases, the tablets or capsules may be the appropriate form of pharmaceutical preparation owing to the prolonged effect obtained when the drug is given orally, in particular in the form of sustained-release tablets.

In the treatment of infectious diseases, such tablets may advantageously contain other active components, as mentioned hereinbefore.

Still another object of the invention is to provide a method of treating patients suffering from infectious diseases, the method comprising administering to adult patients from 0.25 g to 4 g per day, preferably from 0.5 to 3 g per day, of a compound of the formula I or an equivalent amount of a salt or an easily hydrolyzable ester thereof. Preferably, the compound is given in the form of the dosage units aforesaid.

In the following are given some examples on the preparation of intermediates which are illustrative but not limiting for the invention.

[+)] corresponding to German Offenlegungsschrift No. P 26 28 360
[++)] corresponding to German Offenlegungsschrift No. P 26 54 508

PREPARATION 1

3-Deoxy-16deacetoxy-3β,16α-dibromofusidic acid acetoxymethyl ester

Phenyl chloroformate (3.78 ml; 30 mmol) was added dropwise at 0° C. to a stirred solution of sodium bromide (3.09 g; 30 mmol) and 16-epideacetylfusidic acid acetoxymethyl ester (1.73 g; 5 mmol) in dimethylformamide (30 ml). After stirring at 0°–5° C. for 4 hours, the mixture was left at room temperatur for 5 days. On addition of methanolwater 1:1 (45 ml) an oily product precipitated which was repeatedly washed by decantation with methanol-water 1:1, taken up in ether (50 ml), washed with water, dried and evaporated in vacuo. The amorphous residue thus obtained was purified by dry column chromatography on silica gel (petroleum ether-ethyl acetate 9:1) to yield the desired compound as a colourless foam which crystallized from ether-petroleum ether, melting point: 125°–126° C.

PREPARATION 2

3-Deoxy-16-deacetoxy-3β,16α-dibromo-24,25-dihydrofusidic acid acetoxymethyl ester By substituting 16-epideacetyl-24,25-dihydrofusidic acid acetoxymethyl ester for the 16-epideacetylfusidic acid acetoxymethyl ester in the procedure of Preparation 1, 3-deoxy-16-deacetoxy-3β,16α-dibromo24,25-dihydrofusidic acid acetoxymethyl ester was obtained as a colourless foam.

The NMR spectrum (CDCl$_3$) shows signals at δ = 0.77 (s, 3H; C$\underline{H}_3$-18), 0.87 (d,J=5.5, 6H; C$\underline{H}_3$-26 and C$\underline{H}_3$-27), 1.05 (s, 3H; C$\underline{H}_3$-19), 1.08 (d,J=7, 3H; C$\underline{H}_3$-30), 1.43 (s, 3H; C$\underline{H}_3$-32), 2.10 (s, 3H; COC$\underline{H}_3$), 3.46 (m, 1H; C$\underline{H}$-13), 3.60 (bm, 1H; C$\underline{H}$-3), 4.33 (m, 1H; C$\underline{H}$-11), 5.56 (bt, 1H; C$\underline{H}$-16), and 5.80 and 5.90 (dd, J=6, 2H; OC$\underline{H}_2$O) ppm. Tetramethylsilane was used as internal reference.

PREPARATION 3

3,11-Diketo-16-deacetoxy-16α-bromofusidic acid acetoxymethyl ester

To a stirred solution of 16-deacetoxy-16α-bromofusidic acid acetoxymethyl ester (3.05 g; 5 mmol) in acetone (50 ml) was added dropwise at 0° C. 3.12 ml of Jones reagent (solution of 26.72 g of chromic trioxide in 23 ml of concd. sulfuric acid, diluted with water to 100 ml). After the addition was finished, the mixture was stirred at 0°–5° C. for 40 minutes. Water (50 ml) and ethyl acetate (150 ml) were added with stirring, the organic layer was separated, and the aqueous layer extracted with ethyl acetate (25 ml). The combined organic extracts were washed with water (4 × 20 ml), dried, and evaporated in vacuo to afford the desired compound as a colourless foam which failed to crystallize.

PREPARATION 4

3,11-Diketo-16-deacetoxy-16α-bromo-24,25-dihydrofusidic acid acetoxymethyl ester Following the procedure of Preparation 3 but substituting 16-deacetoxy-16α-bromo-24,25-dihydrofusidic acid acetoxymethyl ester for the 16-deacetoxy-16α-bromofusidic acid acetoxymethyl ester, 3,11-diketo-16-deacetoxy-16α-bromo-24,25-dihydrofusidic acid acetoxymehyl ester was obtained as a colourless foam. The NMR spectrum (CDCl$_3$) shows signals at δ = 0.88 (d, J=5.5, 6H; C$\underline{H}_3$-26 and C$\underline{H}_3$-27), 1.04 (s, 3H; C$\underline{H}_3$-18), 1.07 (d, J=7, 3H; C$\underline{H}_3$-30), 1.08 (s, 3H; C$\underline{H}_3$-19), 1.25 (s, 3H; C$\underline{H}_3$-32), 2.14 (s, 3H; COC$\underline{H}_3$), 3.30 (bm, 1H; C$\underline{H}$-13), 5.73 (bt, 1H; C$\underline{H}$-16), and 5.86 and 5.94 (dd, J=6, 2H; OC$\underline{H}_2$O) ppm. Tetramethylsilane was used as internal reference.

PREPARATION 5

3-Epi-16-deacetoxy-16α-bromofusidic acid acetoxymethyl ester

Sodium borohydride (0.17 g) was added at 0° C. to a solution of 3,11-diketo-16-deacetoxy-16α-bromofusidic acid acetoxymethyl ester (1.82 g; 3 mmol) in ethanol (30 ml). After stirring at 0°–5° C. for 10 minutes, another portion of sodium borohydride (0.17 g) was added, and the mixture was stirred at the low temperature for a further 30 minutes. Excess sodium borohydride was removed by addition of acetic acid, the mixture was acidified with diluted aqueous hydrochloric acid, and water (50 ml) was added. The oily precipitate thus obtained was extracted with ether (2 × 25 ml), the ethereal extracts were washed with water until neutral, dried, and evaporated in vacuo to give the desired compound as a colourless foam.

PREPARATION 6

3-Epi-16-deacetoxy-16α-bromo-24,25-dihyrofusidic acid acetoxymethyl ester

This compound was obtained by following the procedure described in Preparation 5 but substituting 3,11-diketo16-deacetoxy-16α-bromo-24,25-dihydrofusidic acid acetoxymethyl ester for the 3,11-diketo-16-deacetoxy-16α-bromofusidic acid acetoxymethyl ester.

The NMR-spectrum (CDCl$_3$) shows signals at δ = 0.77 (s, 3H; C$\underline{H}_3$-18), 0.87(d, J=6, 6H; C$\underline{H}_3$-26 and C$\underline{H}_3$-27), 0.95 (d, J=6, 3H; C$\underline{H}_3$-30), 1.01 (s, 3H; C$\underline{H}_3$-19), 1.42 (s, 3H; C$\underline{H}_3$-32), 2.12 (s, 3H; COC$\underline{H}_3$), 3.10 (b, 1H; C$\underline{H}$-3), 3.42 (bm, 1H; C$\underline{H}$-13), 4.37 (bm, 1H; C$\underline{H}$-11), 5.62 (bt, 1H; C$\underline{H}$-16), and 5.83 and 5.92 (dd, J=6, 2H; OC$\underline{H}_2$O) ppm. Tetramethylsilane was used as internal reference.

PREPARATIONS 7–12

3-O-Mesyl and 3-O-tosyl derivatives of the acetoxymethyl esters of 16-deacetoxy-16α-bromofusidic acid, 3-epi-16-deacetoxy-16α-bromofusidic acid and their corresponding 24,25-dihydro analogues General procedure: To a stirred solution of the starting material (10 mmol; Q$_1$ = H,α-OH or H,β-OH in the below formula) in methylene chloride-pyridine 1:1 (40 ml) was added dropwise at −15° C. a 2 M solution of methanesulfonyl or p-toluenesulfonyl chloride in methylene chloride (15 ml). The mixture was stirred at −15° C. for 1 hour and then kept in the refrigerator overnight. To the mixture was added ice-water (30 ml), and, after stirring for 30 minutes, the organic phase was separated. The aqueous phase was extracted with ether (2 × 40 ml), and the combined organic extracts were washed with 2 N aqueous hydrochloric acid, followed by 0.5 M aqueous sodium bicarbonate and water, dried, and evaporated in vacuo to afford the desired compound as a foam.

The compounds prepared according to the above procedure are listed in table I below:

Table I:

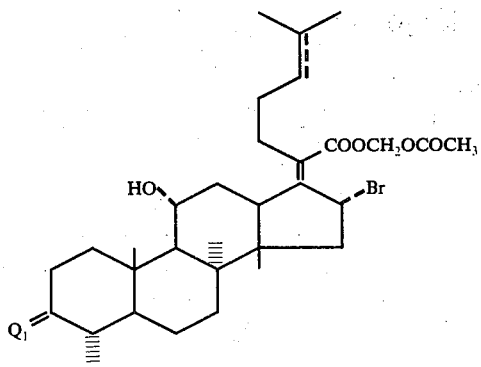

| Example | Q₁ | Resulting compound C-24,24 bond | Mp (° C) | NMR (CDCl₃), chemical shift |
|---|---|---|---|---|
| 7 | H,α-OSO$_2$CH$_3$ | double | 115–116 | δ=3.04(s,3H; OSO$_2$C$\underline{H}_3$) and 4.85(m,1H; C$\underline{H}$-3) ppm |
| 8 | H,β-OSO$_2$CH$_3$ | double | amorphous | δ=3.02(s,3H; OSO$_2$C$\underline{H}_3$) and 4.20(b,1H; C$\underline{H}$-3) ppm |
| 9 | H,α-OSO$_2$CH$_3$ | single | amorphous | δ=3.00(s,3H; OSO$_2$C$\underline{H}_3$) and 4.78(m,1H; C$\underline{H}$-3) ppm |
| 10 | H,β-OSO$_2$CH$_3$ | single | amorphous | δ=3.03(s,3H; OSO$_2$C$\underline{H}_3$) and 4.18(b,1H; C$\underline{H}$-3) ppm |
| 11 | H,α-OSO$_2$–⟨C₆H₄⟩–CH$_3$ | double | amorphous | δ=2.47(s,3H; arom. C$\underline{H}_3$), 4.70(m,1H; C$\underline{H}$-3), 7.37 and 7.87(2d,J=8, 4H; arom. C$\underline{H}$) ppm |
| 12 | H,β-OSO$_2$–⟨C₆H₄⟩–CH$_3$ | single | amorphous | δ=2.45(s,3H; arom.C$\underline{H}_3$), 4.12(b,1H; C$\underline{H}$-3), 7.35 and 7.83(2d, J=8, 4H; arom.C$\underline{H}$) ppm |

PREPARATION 13

3-Deoxy-16-deacetoxy-3α,16α-dibromofusidic acid acetoxymethyl ester

To a solution of 3-epi-16-deacetoxy-16α-bromofusidic acid acetoxymethyl ester (1.22 g; 2 mmol) and triphenylphosphine (1.18 g; 4.5 mmol) in dry ether (25 ml) was added tetrabromomethane (1.33 g; 4 mmol), and the mixture was stirred at room temperature for 18 hours. Precipitated triphenylphosphine oxide was filtered off, washed with dry ether, and the filtrate was evaporated in vacuo. The oily residue thus obtained was purified by dry column chromatography on silica gel (ethyl acetate-petroleum ether 1:9) to give the desired compound as a colourless foam.

PREPARATION 14

3-Deoxy-16-deacetoxy-3α,16α-dibromo-24,25-dihydrofusidic acid acetoxymethyl ester This compound was obtained by substituting 3-epi-16-deacetoxy-16α-bromo-24,25-dihydrofusidic acetoxymethyl ester for the 3-epi-16-deacetoxy-16α-bromofusidic acid acetoxymethyl ester in the procedure of preparation 13.

The invention will be further described in the following Examples which are not to be construed as limiting the invention.

EXAMPLE 1

16-Deacetoxy-16β-(acetylthio)-fusidic acid

A. 16-Deacetoxy-16β-(acetylthio)fusidic acid acetoxymethyl ester

To a solution of 16-deacetoxy-16α-bromofusidic acid acetoxymethyl ester (4.88 g; 8 mmol) in dimethylformamide (50 ml) was added potassium thioacetate (1.47 g; 12 mmol), and the mixture was stirred at room temperature for 20 hours. After the dilution with ether (200 ml), the reaction mixture was washed with water (2 × 50 ml, 4 × 25 ml), and the organic phase was dried and evaporated in vacuo to afford 4.8 g of the desired compound as a colourless foam.

B. 16-Deacetoxy-16β-(acetylthio)fusidic acid

Potassium carbonate (2.22 g; 16 mmol) was added to an ice-cold solution of the above 16-deacetoxy-16β-(acetylthio)fusidic acid acetoxymethyl ester (4.8 g; ca. 8 mmol) in methanol (80 ml), and the mixture was stirred at 0°–5° C. for 20 minutes. The reaction mixture was poured into ice-water (ca. 250 ml), acidified with 4 N hydrochloric acid, and the oily precipitate thus formed was extracted with ether (2 × 100 ml). The combined ethereal extracts were washed with water until neutral, dried, and evaporated in vacuo. The resulting amorphous residue crystallized from diisopropyl ether to yield 3.22 g of 16-deacetoxy-16β-(acetylthio)fusidic acid, melting point: 208°–210° C. Two recrystallizations from methanol-diisopropyl ether afforded the analytically pure compound, melting point: 213°–214° C.

EXAMPLE 2

16-Deacetoxy-16β-(benzoylthio)fusidic acid

A. 3-O-Formyl-16-deacetoxy-16β-(benzoylthio)fusidic acid benzoyloxymethyl ester

By following the procedure described in Example 1A, but substituting 3-O-formyl-16-deacetoxy-16α-bromofusidic acid benzoyloxymethyl ester for the 16-deacetoxy-16α-bromofusidic acid acetoxymethyl ester and potassium thiobenzoate for the potassium thioacetate, 3-O-formyl-16-deacetoxy-16β-(benzoylthio)fusidic acid benzoyloxymethyl ester, melting point: 102°–104° C., was obtained.

B. 16-Deacetoxy-16β-(benzoylthio)fusidic acid

To a suspension of 3-O-formyl-16-deacetoxy-16β-(benzoylthio)fusidic acid benzoyloxymethyl ester (9.84 g; 13 mmol) in methanol (260 ml) was added potassium carbonate (3.64 g; 26 mmol), and the mixture was stirred at room temperature for 2 hours. The clear solution thus obtained was diluted with ether (750 ml), water (250 ml) was added, and the stirred mixture was acidified with 4 N aqueous hydrochloric acid. The organic phase was separated and the aqueous phase reextracted with ether (100 ml). The combined organic extracts were washed with water until neutral, dried, and evaporated in vacuo. The amorphous residue thus obtained crystallized from diisopropyl ether to yield 6.36 g of 16-deacetoxy-16β-(benzoylthio)fusidic acid, showing a melting interval between 160°–172° C. Recrystallization from methanol-diisopropyl ether afforded the analytically pure compound, its melting point still being undefined.

EXAMPLE 3

16-Deacetoxy-16β-acetylthio-24,25-dihydrofusidic acid

A.
3-O-Formyl-16-deacetoxy-16β-acetylthio-24,25-dihydrofusidic acid acetoxymethyl ester To a solution of 3-O-formyl-16-deacetoxy-16α-bromo-24,25-dihydrofusidic acid acetoxymethyl ester (31.98 g; 50 mmol) in dimethylformamide (200 ml) was added potassium thioacetate (8.55 g; 75 mmol), and the mixture was stirred at room temperature for 18 hours. After dilution with ether (800 ml), the mixture was washed with water (2 × 200 ml, 4 × 100 ml), and the organic layer was dried and concentrated to a volume of about 150 ml at reduced pressure. The colourless, crystalline product which precipitated was kept in the refrigerator for 2 hours, then filtered off, washed with ether, and dried to yield 21.50 g of the desired compound, melting point: 166°–168° C. After dilution of the mother liquor with diisopropyl ether (75 ml) and concentration to about 50 ml, a second crop of crystalline product was obtained. The crystals were collected, washed with diisopropyl ether, and dried to afford 5.24 g of 3-O-formyl-16-deacetoxy-16β-acetylthio-24,25-dihydrofusidic acid acetoxymethyl ester, melting point: 164°–166° C.

B. 16-Deacetoxy-16β-acetylthio-24,25-dihydrofusidic acid

To a suspension of 3-O-formyl-16-deacetoxy-16β-acetylthio-24,25-dihydrofusidic acid acetoxymethyl ester (25.4 g; 40 mmol) in methanol (200 ml) was added 4 N aqueous hydrochloric acid, and the mixture was stirred at room temperature for 24 hours. The clear solution thus obtained was poured into water (600 ml) and the resulting oily precipitate was extracted with ether (2 × 200 ml). The combined ethereal extracts were washed with water until neutral, dried, and concentrated to about 50 ml. Diisopropyl ether (200 ml) was added, and, after further concentration to about 150 ml, a colourless product began to crystallize. The mixture was left at room temperature for 2 hours, and the crystals were filtered off, washed with diisopropyl ether, and dried to give 19.64 g of 16-deacetoxy-16β-acetylthio-24,25-dihydrofusidic acid, melting point: 189°–191° C. Two recrystallizations from methanol-diisopropyl ether afforded the analytical sample, melting point: 193°–194° C.

EXAMPLE 4

16-Deacetoxy-16β-benzoylthio-24,25-dihydrofusidic acid

A. 16-Deacetoxy-16β-benzoylthio-24,25-dihydrofusidic acid acetoxymethyl ester

By substituting 16-deacetoxy-16α-bromo-24,25-dihydrofusidic acid acetoxymethyl ester from the 16-deacetoxy-16α-bromofusidic acid acetoxymethyl ester and potassium thiobenzoate for the corresponding thioacetate in the procedure of Example 1A, 16-deacetoxy-16β-benzoylthio-24,25-dihydrofusidic acid acetoxymethyl ester was obtained.

B. 16-Deacetoxy-16β-benzoylthio-24,25-dihydrofusidic acid

Following the procedure described in Example 1B, but substituting 16-deacetoxy-16β-benzoylthio-24,25-dihydrofusidic acid acetoxymethyl ester for the 16-deacetoxy-16β-(acetylthio)fusidic acid acetoxymethyl ester, 16-deacetoxy-16β-benzoylthio-24,25-dihydrofusidic acid, melting interval 165°–175° C., was obtained.

EXAMPLE 5–8

3-Keto-16-deacetoxy-16β-(acetylthio)fusidic acid, 11-keto-16-deacetoxy-16β-(acetylthio)fusidic acid and their corresponding 24,25-dihydro derivatives A. By substituting the acetoxymethyl esters of 3-keto-16-deacetoxy-16α-bromofusidic acid, 3-O-formyl-11-keto-16-deacetoxy-16α-bromofusidic acid and their corresponding 24,25-dihydro derivatives for the 3-O-formyl-16-deacetoxy-16α-bromo-24,25-dihydrofusidic acid acetoxymethyl ester in the procedure of Example 3A, the 16β-acetylthio esters shown in the table II below were obtained.

B. Following the procedure described in Example 3B but substituting the 16β-acetylthio esters indicated in table I for the 3-O-formyl-16-deacetoxy-16β-acetylthio-24,25-dihydrofusidic acid acetoxymethyl ester, the 16β-acetylthio acids listed in table II were obtained.

Table II:

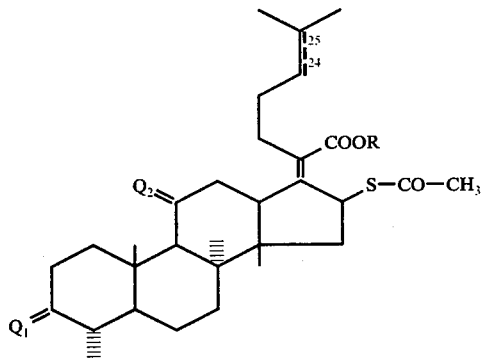

| Example | Q₁ | Q₂ | R | C-24,25 bond | (° C) |
|---|---|---|---|---|---|
| 5A | O | H,α-OH | CH₂OCOCH₃ | double | 143–144 |
| 6A | O | H,α-OH | CH₂OCOCH₃ | single | 146–147 |
| 7A | H,α-OCHO | O | CH₂OCOCH₃ | double | 136–137 |
| 8A | H,α-OCHO | O | CH₂OCOCH₃ | single | 167–168 |
| 5B | O | H,α-OH | H | double | amorphous |
| 6B | O | H,α-OH | H | single | amorphous |
| 7B | H,α-OH | O | H | double | 193–194 |
| 8B | H,α-OH | O | H | single | 196–197 |

EXAMPLES 9–12

3-Keto-16-deacetoxy-16β-(benzoylthio)fusidic acid, 11-keto-16-deacetoxy-16β-(benzoylthio)fusidic acid and their corresponding 24,25-dihydro derivatives A. By following the procedure described in Example 3A but substituting the acetoxymethyl esters of 3-keto-16-deacetoxy-16α-bromofusidic acid, 3-O-formyl-11-keto-16-deacetoxy-16α-bromofusidic acid and their corresponding 24,25-dihydro derivatives for the 3-O-formyl-16-deacetoxy-16α-bromo-24,25-dihydrofusidic acid acetoxymethyl ester and potassium thiobenzoate for the corresponding thioacetate, the 16β-benzoylthio esters shown in table III below were obtained.

B. By substituting the 16β-benzoylthio esters shown in table III for the 3-O-formyl-16-deacetoxy-16β-acetylthio-24,25-dihydrofusidic acid acetoxymethyl ester in the procedure of Example 3B, the 16β-benzoylthio acids listed in table III were obtained.

Table III:

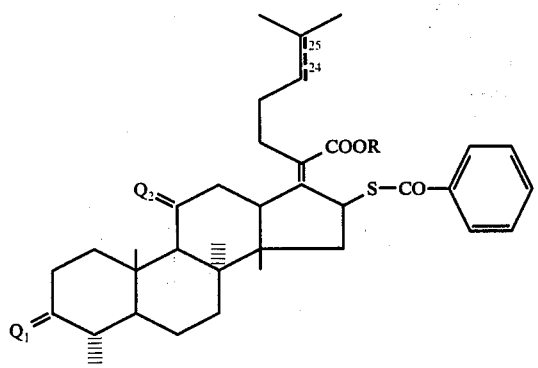

| Example | Q₁ | Q₂ | R | C-24,25 bond | Mp (° C) |
|---|---|---|---|---|---|
| 9A | O | H,α-OH | CH₂OCOCH₃ | double | amorphous |
| 10A | O | H,α-OH | CH₂OCOCH₃ | single | amorphous |
| 11A | H,α-OCHO | O | CH₂OCOCH₃ | double | amorphous |
| 12A | H,α-OCHO | O | CH₂OCOCH₃ | single | amorphous |
| 9B | O | H,α-OH | H | double | 227–228 |
| 10B | O | H,α-OH | H | single | 198–199 |
| 11B | H,α-OH | O | H | double | 220–222 |
| 12B | H,α-OH | O | H | single | 216–218 |

EXAMPLES 13–16

3,11-Diketo-16-deacetoxy-16β-(acetylthio)fusidic acid, 3-epi-16-deacetoxy-16β-(acetylthio)fusidic acid and their corresponding 24,25-dihydro derivatives.

A. By substituting the acetoxymethyl esters of 3,11-diketo-16-deacetoxy-16α-bromofusidic acid, 3-epi-16-deacetoxy-16α-bromofusidic acid and their corresponding 24,25-dihydro derivatives for the 16-deacetoxy-16α-bromofusidic acid acetoxymethyl ester in the procedure of Example 1A, the 16β-acetylthio esters shown in table IV below were obtained.

B. Following the procedure of Example 1B but substituting the 16β-acetylthio esters indicated in table IV for the 16-deacetoxy-16β-(acetylthio)fusidic acid acetoxymethyl ester, the 16β-acetylthio acids listed in table IV were obtained.

Table IV:

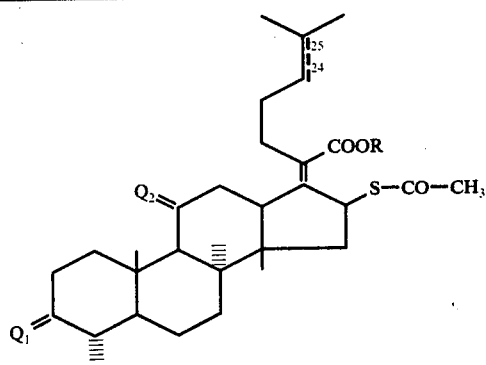

| Example | Q₁ | Q₂ | R | C-24,25 bond | Mp(° C) |
|---|---|---|---|---|---|
| 13A | O | O | CH₂OCOCH₃ | double | amorphous |
| 14A | H,β-OH | H,α-OH | CH₂OCOCH₃ | double | 154–156 |
| 15A | O | O | CH₂OCOCH₃ | single | amorphous |
| 16A | H,β-OH | H,α-OH | CH₂OCOCH₃ | single | 177–179 |
| 13B | O | O | H | double | 200–202 |
| 14B | H,β-OH | H,α-OH | H | double | amorphous |
| 15B | O | O | H | single | 220–222 |
| 16B | H,β-OH | H,α-OH | H | single | amorphous |

EXAMPLES 17–20

3-O-Mesyl derivatives of 16-deacetoxy-16β-(acetylthio)fusidic acid, 3-epi-16-deacetoxy-16β-(acetylthio)fusidic acid and their corresponding 24,25-dihydro compounds A. Following the procedure described in Example 1 A but substituting the acetoxymethyl esters of 3-O-mesyl-16-deacetoxy-16α-bromofusidic acid, 3-epi-O-mesyl-16-deacetoxy-16α-bromofusidic acid and their corresponding 24,25-dihydro derivatives for the 16-deacetoxy-16α-bromofusidic acid acetoxymethyl ester and decreasing the reaction time from 20 hours to 4–8 hours, the 16β-acetylthio esters listed in table V below were obtained.

B. By substituting the 16β-acetylthio esters listed in table V for the 16-deacetoxy-16β-(acetylthio)fusidic acid acetoxymethyl ester in the procedure of Example 1 B, the 16β-acetylthio acids indicated in table V were obtained.

Table V:

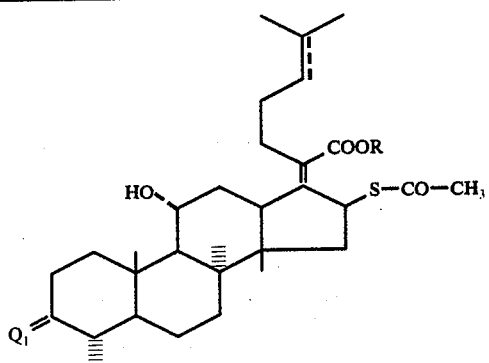

| Example | Q₁ | R | C-24, 25 bond | Mp(° C) |
|---|---|---|---|---|
| 17A | H,α-OSO₂CH₃ | CH₂OCOCH₃ | double | 106–108 |
| 18A | H,β-OSO₂CH₃ | CH₂OCOCH₃ | double | amor- |

Table V:-continued

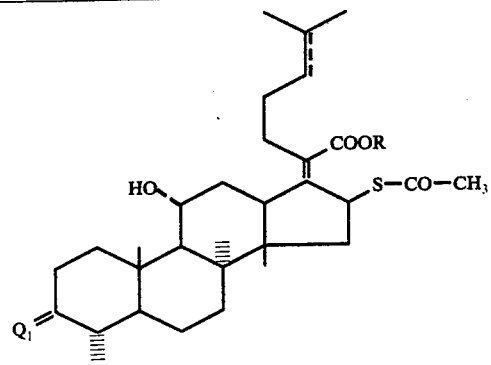

| Example | Q₁ | R | C-24, 25 bond | Mp(° C) |
|---|---|---|---|---|
| | | | | phous |
| 19A | H,α-OSO₂CH₃ | CH₂OCOCH₃ | single | 110–112 |
| 20A | H,β-OSO₂CH₃ | CH₂OCOCH₃ | single | amorphous |
| 17B | H,α-OSO₂CH₃ | H | double | amorphous |
| 18B | H,β-OSO₂CH₃ | H | double | 153–154 |
| 19B | H,α-OSO₂CH₃ | H | single | amorphous |
| 20B | H,β-OSO₂CH₃ | H | single | 150–151 |

EXAMPLE 21–24

3-Bromo derivatives of 3-deoxy-16-deacetoxy-16β-(acetylthio)fusidic acid and its 24,25-dihydro compound.

A. By following the procedure of Example 1 A but substituting the acetoxymethyl esters of 3-deoxy-16-deacetoxy-3α,6α-dibromofusidic acid, 3-deoxy-16-deacetoxy-3β,16α-dibromofusidic acid, and their corresponding 24,25-dihydro derivatives for the 16-deacetoxy-16α-bromofusidic acid acetoxymethyl ester and decreasing the reaction time from 20 hours to 4–8 hours, the 16β-acetylthio esters shown in table VI below were obtained.

B. By substituting the 16β-acetylthio esters shown in table VI for the 16-deacetoxy-16β-(acetylthio)fusidic acid acetoxymethyl ester in the procedure of Example 1 B, the 16β-acetylthio acids listed in table VI were obtained.

Table VI:

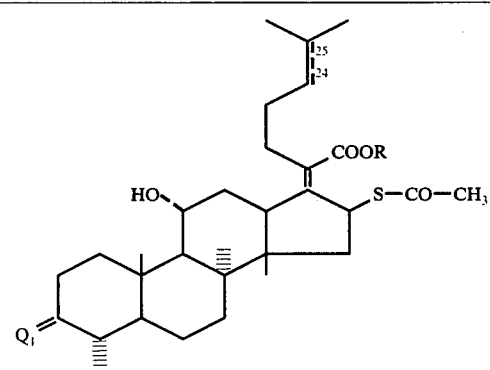

| Example | Q₁ | R | C-24, 25 bond | Mp (° C) |
|---|---|---|---|---|
| 21A | H,β-Br | CH₂OCOCH₃ | double | amorphous |
| 22A | H,β-Br | CH₂OCOCH₃ | single | amorphous |
| 23A | H,α-Br | CH₂OCOCH₃ | double | amorphous |
| 24A | H,α-Br | CH₂OCOCH₃ | single | amorphous |
| 21B | H,β-Br | H | double | 183–184 |
| 22B | H,β-Br | H | single | 179–180 |
| 23B | H,α-Br | H | double | amorphous |
| 24B | H,α-Br | H | single | amorphous |

EXAMPLE 25

3-Deoxy-3β-bromo-16-deacetoxy-16β-(acetylthio)fusidic acid

A.

3-Deoxy-3β-bromo-16-deacetoxy-16β-(acetylthio)fusidic acid acetoxymethyl ester

Phenyl N,N-dimethylformamide bromide was prepared by dropwise addition of phenyl chloroformate (6.5 ml; 50 mmol) to a stirred solution of sodium bromide (5.14 g; 50 mmol) in dimethylformamide at 0°–5° C. Sodium chloride precipitated, and the resulting suspension was stirred at 0°–5° C. for 4 hours and then at room temperature overnight. The mixture was cooled to 0° C. and 16-deacetoxy-16β-(acetylthio)fusidic acid acetoxymethyl ester (6.07 g; 10 mmol) was added with stirring. After stirring at 0°–5° C. for 4 hours, the mixture was left at room temperature for a further 4 days. On dilution of the stirred reaction mixture with methanol-water 1:1 (75 ml) an oily product precipitated, which was washed repeatedly by decantation with methanol-water 1:1 and finally taken up in ether, dried, and evaporated in vacuo. The amorphous residue thus obtained was purified by dry column chromatography on silica gel (petroleum ether-ethyl acetate 85:15) to give the desired compound as a colourless foam.

B.

3-Deoxy-3β-bromo-16-deacetoxy-16β-(acetylthio)fusidic acid

To an icecold solution of the above ester (2.67 g; 4 mmol) in methanol (40 ml) was added potassium carbonate (0.56 g; 4 mmol) and the mixture was stirred at 0° C. for 20 minutes. After addition of ether (120 ml) and water (80 ml), the stirred mixture was acidified with diluted hydrochloric acid, and the organic phase was separated. The aqueous phase was reextracted with ether (40 ml), and the combined organic phases were washed with water (4 × 25 ml), dried, and evaporated in vacuo. The resulting amorphous residue crystallized from ether-petroleum ether to give 3-deoxy-3β-bromo-16-deacetoxy-16β-(acetylthio)fusidic acid, melting point: 182°–184° C.

EXAMPLE 26

3-Deoxy-3β-bromo-16-deacetoxy-16β-acetylthio-24,25-dihydrofusidic acid

By following the procedure described in Example 25 but substituting 16-deacetoxy-16β-acetylthio-24,25-dihydrofusidic acid acetoxymethyl ester for the 16-deacetoxy-16β-(acethylthio)fusidic acid acetoxymethyl ester, 3-deoxy-3β-bromo-16-deacetoxy-16β-acetylthio-24,25-dihydrofusidic acid, melting point: 178°–180° C., was obtained.

EXAMPLE 27

3-Deoxy-3β-azido-16-deacetoxy-16β(acetylthio)fusidic acid

A.

3-Deoxy-3β-azido-16-deacetoxy-16β-(acetylthio)fusidic acid acetoxymethyl ester

A solution of 3-O-mesyl-16-deacetoxy-16β-(acetylthio)fusidic acid acetoxymethyl ester (2.32 g; 3.4 mmol) and lithium azide (0.33 g; 6.8 mmol) in dimethylformamide (20 ml) was stirred at room temperature for 48 hours. The mixture was diluted with ether (80 ml), washed with water (4 × 20 ml), and the organic phase was dried and evaporated in vacuo to give the desired compound as a colourless foam.

The IR spectrum (KBr) shows a strong band at $\nu = 2100$ cm$^{-1}$ (N$_3$).

B.

3-Deoxy-3β-azido-16-deacetoxy-16β-(acetylthio)fusidic acid

To a solution of the amorphous 3-deoxy-3β-azido-16-deacetoxy-16β-(acetylthio)fusidic acid acetoxymethyl ester (2.14 g; ≈ 3.4 mmol) in methanol (34 ml) was added at 0° C. potassium carbonate (0.94 g; 6.8 mmol), and the mixture was stirred at the low temperature for 20 minutes. After addition of water (100 ml) and acidification with 4 N aqueous hydrochloric acid, the oily precipitate thus formed was extracted with ether (2 × 50 ml). The combined ethereal extracts were washed with water until neutral, dried, and evaporated in vacuo. The resulting amorphous residue was purified by dry column chromatography on silica gel (ether-petroleum ether-acetic acid 50:50:0.5) to afford the desired compound as a colourless foam which crystallized from diisopropyl ether, melting point: 185°–187° C.

EXAMPLES 28–34

3β-Substituted derivatives of 3-deoxy-16-deacetoxy-16β-(acetylthio)fusidic acid and its corresponding 24,25-dihydro compound A. By reacting 3-O-mesyl-16-deacetoxy-16β-(acetylthio)fusidic acid acetoxymethyl ester or its 24,25-dihydro derivative with the nucleophilic agents indicated in table VII and using the same method as described in Example 27 A, the 3β-substituted esters listed in table VII below were obtained.

B. Following the procedure of Example 27 B but substituting the 3β-substituted esters shown in table VII for the 3-deoxy-3β-azido-16-deacetoxy-16β-(acetylthio)fusidic acid acetoxymethyl ester, the 3β-substituted acids listed in table VII were obtained.

Table VII

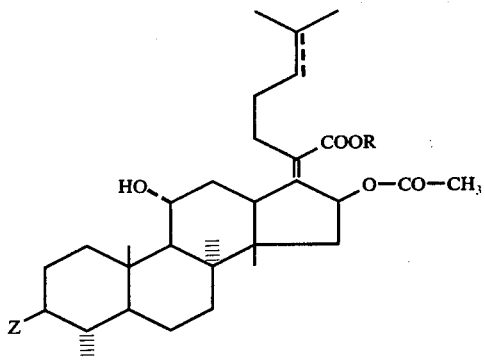

| Example | Nucleophilic agent | Resulting compound Z | R | C-24,25 bond | Mp(° C) |
|---|---|---|---|---|---|
| 28A | Lithium azide | N₃ | CH₂OCOCH₃ | single | 105–107 |
| 29A | Tetrabutylammonium chloride | Cl | CH₂OCOCH₃ | double | amorphous |
| 30A | Tetrabutylammonium chloride | Cl | CH₂OCOCH₃ | single | amorphous |
| 31A | Tetrabutylammonium bromide | Br | CH₂OCOCH₃ | double | amorphous |
| 32A | Tetrabutylammonium bromide | Br | CH₂OCOCH₃ | single | amorphous |
| 33A | Sodium iodide | I | CH₂OCOCH₃ | single | amorphous |
| 34A | Lithium nitrite | NO₂ | CH₂OCOCH₃ | single | amorphous |
| 28B | | N₃ | H | single | 179–180 |
| 29B | | Cl | H | double | 186–187 |
| 30B | | Cl | H | single | 202–203 |
| 31B | | Br | H | double | 182–184 |
| 32B | | Br | H | single | 178–180 |
| 33B | | I | H | single | amorphous |
| 34B | | NO₂ | H | single | 210–213 |

EXAMPLE 35

3-Deoxy-3α-azido-16-deacetoxy-16β-(acetylthio)fusidic acid

A.

3-Deoxy-3α-azido-16-deacetoxy-16β-(acetylthio)fusidic acid acetoxymethyl ester

3-Epi-O-mesyl-16-deacetoxy-16β-(acetylthio)fusidic acid acetoxymethyl ester (1,50 g; 2.2 mmol) and lithium azide (0.22 g; 4.4 mmol) were dissolved in dimethylformamide (15 ml), and the resulting solution was stirred at 50°–55° C. for 48 hours. After dilution with ether (60 ml), the mixture was washed with water (4 × 15 ml), and the remaining organic phase was dried and evaporated in vacuo. The amorphous residue thus obtained was purified by dry column chromatography on silica gel (petroleum ether-ethyl acetate 85:15) to yield the desired compound as a colourless foam.

The IR spectrum (KBr) shows a strong band at $\nu$ = 2100 cm$^{-1}$ (N₃).

B.

3-Deoxy-3α-azido-16-deacetoxy-16β-(acetylthio)fusidic acid

To an ice-cold solution of 3-deoxy-3α-azido-16-deacetoxy-16β-(acetylthio)fusidic acid acetoxymethyl ester (0.44 g; 0.7 mmol) in methanol (7 ml) was added potassium carbonat (0.19 g; 1.4 mmol), and the mixture was stirred at 0° C. for 20 minutes. Water (35 ml) and 2 N aqueous hydrochloric acid (0.8 ml) was added, and the oily precipitate which formed was extracted with ether (2 × 25 ml). The combined ethereal extracts were washed with water until neutral, dried, and evaporated in vacuo to give the desired compound which crystallized from ether-petroleum ether.

The NMR spectrum (CDCl₃) shows signals at $\delta$ = 5.18 (d, J=8, 1H; C$\underline{H}$-16), 5.10 (m, 1H; C$\underline{H}$-24), 4.35 (m, 1H; C$\underline{H}$-11), 3.70 (m, 1H; C$\underline{H}$3), 3.15 (bm, 1H; C$\underline{H}$-13), 2.32 (s, 3H; COC$\underline{H}$₃), 1.67 and 1.60 (2 bs, 6H; C$\underline{H}$₃-26 and C$\underline{H}$₃-27), 1.38 (s, 3H; C$\underline{H}$₃-32), 0.98 (s, 3H; C$\underline{H}$₃-9), and 0.92 (s, 3H; C$\underline{H}$₃-18) ppm. Tetramethylsilane was used as internal reference.

EXAMPLE 36

3-Deoxy-3α-azido-16-deacetoxy-16β-acetylthio-24,25-dihydrofusidic acid

A.

3-Deoxy-3α-azido-16-deacetoxy-16β-acetylthio-24,25-dihydrofusidic acid acetoxymethyl ester By substituting 3-epi-O-mesyl-16-deacetoxy-16β-acetylthio-24,25-dihydrofusidic acid acetoxymethyl ester for the 3-epi-O-mesyl-16-deacetoxy-16β-(acetylthio)fusidic acid acetoxymethyl ester in the procedure of Example 35 A, 3-deoxy-3α-azido-16-deacetoxy-16β-acetylthio-24,25-dihydrofusidic acid acetoxymethyl ester, melting point: 165°–167° C., was obtained.

B.

3-Deoxy-3α-azido-16-deacetoxy-16β-acetylthio-24,25-dihydrofusidic acid

This compound, melting point: 163°–165° C., was obtained by following the procedure of Example 35 B but substituting 3-deoxy-3α-azido-16-deacetoxy-16β-acetylthio-24,25-dihydrofusidic acid acetoxymethyl ester for the 3-deoxy-3α-azido-16-deacetoxy-16β-(acetylthio)fusidic acid acetoxymethyl ester.

EXAMPLES 37–38

3-Deoxy-3α-chloro-16-deacetoxy-16β-(acetylthio)fusidic acid and its corresponding 24,25-dihydro derivative A. Following the procedures of Examples 35 A and 36 A but substituting tetrabutylammonium chloride for the lithium azide, the 3α-chloro esters shown in table VIII below were obtained.

B. By substituting the 3α-chloro esters shown in table VIII for the 3-deoxy-3α-azido-16-deacetoxy-16β-(acetylthio)fusidic acid acetoxymethyl ester in the procedure of Example 35 B, the 3α-chloro acids listed in table VIII were obtained.

Table VIII:

| Example | R | Resulting compound C-24,25 bond | Mp (° C) |
|---|---|---|---|
| 37 A | CH₂OCOCH₃ | double | amorphous |
| 38 A | CH₂OCOCH₃ | single | amorphous |
| 37 B | H | double | amorphous |
| 38 B | H | single | 211–212 |

EXAMPLE 39

3-Deoxy-3β-fluoro-16-deacetoxy-16β-(acetylthio)fusidic acid

To a solution of 3-deoxy-3α-bromo-16-deacetoxy-16β-(acetylthio)fusidic acid acetoxymethyl ester (0.68 g; 1 mmol) in acetonitrile (10 ml) was added silver fluoride (0.50 g; 4 mmol), and the resulting suspension was stirred for 20 hours in the dark. After addition of ethyl acetate (20 ml), the insoluble material was filtered off, and the filtrate was evaporated in vacuo. The amorphous residue thus obtained was dissolved in methanol (10 ml), potassium carbonate (0.28 g; 2 mmol) was added, and the mixture was stirred at 0°–5° C. for 20 minutes. Water (30 ml) was added, and, after acidification with 1 N hydrochloric acid, the oily precipitate which formed was extracted with ether (2 × 20 ml). The combined ethereal extracts were washed twice with water, dried, and evaporated in vacuo. The resulting amorphous product was purified by dry column chromatography on silica gel (ether-petroleum ether-acetic acid 50:50:0.5) to yield the desired product as a foam.

EXAMPLE 40

3-Deoxy-3β-fluoro-16-deacetoxy-16β-acetylthio-24,25-dihydrofusidic acid

This compound was obtained by following the procedure of Example 39 but substituting 3-deoxy-3α-bromo-16-deacetoxy-16β-acetylthio-24,25-dihydrofusidic acid acetoxymethyl ester for the 3-deoxy-3α-bromo-16-deacetoxy-16β-(acetylthio)-fusidic acid acetoxymethyl ester.

EXAMPLE 41

3-Epi-O-tosyl-16-deacetoxy-16β-acetylthio-24,25-dihydrofusidic acid

A.

3-Epi-O-tosyl-16-deacetoxy-16β-acetylthio-24,25-dihydrofusidic acid acetoxymethyl ester This compound was obtained by substituting 3-epi-O-tosyl-16-deacetoxy-16α-bromo-24,25-dihydrofusidic acid acetoxymethyl ester for the 16-deacetoxy-16α-bromofusidic acid acetoxymethyl ester in the procedure of Example 1A.

B.

3-Epi-O-tosyl-16-deacetoxy-16β-acetylthio-24,25-dihydrofusidic acid

Following the procedure described in Example 1 B but substituting 3-epi-O-tosyl-16-deacetoxy-16β-acetylthio-24,25-dihydrofusidic acid acetoxymethyl ester for the 16-deacetoxy-16β-(acetylthio)-fusidic acid acetoxymethyl ester, 3-epi-O-tosyl-16-deacetoxy-16β-acetylthio-24,25-dihydrofusidic acid, melting point: 131°–133° C., was obtained.

EXAMPLE 42

16-Deacetoxy-16β-acetylthio-24,25-dihydrofusidic acid

A. 16-Deacetoxy-16β-(acetylthio)fusidic acid benzyl ester

Potassium thioacetate (0.69 g; 6 mmol) was added to a solution of 16-deacetoxy-16α-bromofusidic acid benzyl ester (2.51 g; 4 mmol) in dimethylformamide (20 ml), and the mixture was stirred at room temperature for 16 hours. After dilution with ether (80 ml), the mixture was washed with water (4 × 20 ml), and the organic phase was dried and evaporated at reduced pressure to yield the desired compound as a yellowish foam.

The NMR spectrum (CDCl₃) shows signals at $\delta$ = 7.35 (s, 5H; arom. C$\underline{H}$), 5.10 (m, 1H; C$\underline{H}$-24), 5.03 (ABq, J=12, 2H; OC$\underline{H}_2$C₆H₅), 5.02 (d, J=8; C$\underline{H}$-16), 4.41 (m, 1H; C$\underline{H}$-11), 3.71 (m, 1H; C$\underline{H}$-3), 3.03 (bm, 1H; C$\underline{H}$-13), 2.22 (s, 3H; COC$\underline{H}_3$), 1.65 and 1.53 (2 bs, 6H; C$\underline{H}_3$-26 and C$\underline{H}_3$-27), 1.37 (s, 3H; C$\underline{H}_3$-32), 0.97 (s, 3H; C$\underline{H}_3$-19), 0.90 (s, 3H; C$\underline{H}_3$-18), and 0.89 (d, J=7, 3H; C$\underline{H}_3$-30), ppm. Tetramethylsilane was used as internal reference.

B. 16-Deacetoxy-16β-acetylthio-24,25-dihydrofusidic acid

10% Palladium on carbon catalyst (0.4 g) was added to a solution of the above 16-deacetoxy-16β-(acetylthio)fusidic acid benzyl ester (1.25 g; 2 mmol) in ethanol (15 ml), and the mixture was shaken in a hydrogen atmosphere. After the consumption of hydrogen had ceased, the catalyst was filtered off and washed with ethanol. The combined filtrate and washings were evaporated in vacuo, and the resulting residue was crystallized from ether-diisopropyl ether to afford the desired compound, melting point: 191°–193° C.

EXAMPLES 43–54

Further 16-deacetoxy-16β-(acylthio)fusidic acids

General procedure: To a solution of 16-deacetoxy-16α-bromofusidic acid acetoxymethyl ester (2.44 g; 4 mmol) in dimethylformamide (25 ml) was added a sodium or potassium salt of the corresponding thiolcarboxylic acid (6 mmol; see table IX), and the mixture was stirred at room temperature for 18 hours. After dilution with ethyl acetate (100 ml), the mixture was washed with water (4 × 25 ml), dried, and evaporated in vacuo. The resulting residue was dissolved in methanol (40 ml), potassium carbonate (1.12 g; 8 mmol) was added, and the mixture was stirred at 0°–5° C. for 20 minutes. Water (120 ml) was added to the reaction mixture, and after acidification with diluted hydrochloric acid, the oily precipitate thus obtained was extracted with ethyl acetate (2 × 50 ml). The combined organic extracts were washed with water until neutral, dried, and evaporated in vacuo to yield the desired compound. Using the above procedure, the 16-deacetoxy-16β-(acylthio)fusidic acids shown in table IX were obtained.

Table IX:

| Example | Thiolcarboxylic acid | Resulting compound R |
|---|---|---|
| 43 | Thiopropionic acid | CH₂CH₃ |
| 44 | Thiobutyric acid | CH₂CH₂CH₃ |
| 45 | Thioisovaleric acid | CH₂CH(CH₃)₂ |
| 46 | Thiohexanoic acid | CH₂(CH₂)₃CH₃ |
| 47 | Thio-p-toluic acid | —C₆H₄—CH₃ |
| 48 | p-Nitrothiobenzoic acid | —C₆H₄—NO₂ |
| 49 | Pyridine-2-thiocarboxylic acid | 2-pyridyl |
| 50 | Furane-2-thiocarboxylic acid | 2-furyl |
| 51 | thiophene-2-thiocarboxylic acid | 2-thienyl |
| 52 | 3-methylisoxazolyl-5-thio carboxylic acid | 3-methylisoxazol-5-yl |

Table IX:-continued

| Example | Thiolcarboxylic acid | Resulting compound R |
|---|---|---|
| 53 | Thiazole-5-thiocarboxylic acid | thiazol-5-yl |
| 54 | 1-Methyl-1,2,3-triazole-5-thiocarboxylic acid | 1-methyl-1,2,3-triazol-5-yl |

EXAMPLES 55–62

Potassium and sodium salts of a number of 16-deacetoxy-16β-acylthio acids of formula I Crystalline potassium and/or sodium salts of the compounds described in Examples 1–6, and 16 were obtained by the following procedure: To a solution of the corresponding acid (10 mmol) in an appropriate, inert solvent (50–100 ml) was added a 1 N solution of potassium or sodium 2-ethylhexanoate in the same solvent (15 ml), and, almost immediately, a crystalline product began to precipitate. The mixture was kept at room temperature for 2 hours, the crystals were filtered off, washed with acetone, and dried to give the pure potassium or sodium salt of the desired compound.

The salts prepared by this method are listed in table X. Microanalysis, IR and NMR data obtained for these compounds are in agreement with their structures.

Table X:

| Example | Q₁ | R₁ | A | C-24,25 bond | Solvent used | Acid described in Example |
|---|---|---|---|---|---|---|
| 55 | H,α-OH | CH₃ | K | double | acetone | 1 |
| 56 | H,α-OH | C₆H₅ | Na | double | ether | 2 |
| 57 | H,α-OH | CH₃ | K | single | acetone | 3 |
| 58 | H,α-OH | C₆H₅ | Na | single | ether | 4 |
| 59 | H,α-OH | C₆H₅ | K | single | ethyl | 4 |

Table X:-continued

|  |  | Resulting compound |  |  | Acid |
|---|---|---|---|---|---|
| Example | $Q_1$ | $R_1$ | A | C-24,25 bond | Solvent used | described in Example |
| 60 | O | CH₃ | K | double | acetate acetone | 5 |
| 61 | O | CH₃ | K | single | acetone | 6 |
| 62 | H,β-OH | CH₃ | K | single | acetone | 16 |

EXAMPLE 63

| Cream | |
|---|---|
| 16-Deacetoxy-16β-acetylthio-24,25-dihydro-fusidic acid | 20 g |
| Petrolatum | 150 g |
| Liquid paraffin | 150 g |
| Spermaceti | 50 g |
| Sorbitan monopalmitate | 50 g |
| Polyoxyethylene sorbitan monopalmitate | 50 g |
| Water | 530 g |
| | 1000 g |

Heat petrolatum, paraffin, spermaceti, sorbitan-monopalmitate, and polyoxyethylene sorbitan monopalmitate to 70° C. and add slowly the water at 72° C. with agitation. Continue agitation until the cream has cooled. Triturate 16-deacetoxy-16β-acetylthio-24,25-dihydrofusidic acid into the cream base and homogenize using a roller mill. Fill the cream into laquered aluminium collapsible tubes.

| Cream | |
|---|---|
| 3-Deoxy-3β-bromo-16-deacetoxy-16β-acetylthio-24,25-dihydrofusidic acid | 20 g |
| Petrolatum | 150 g |
| Liquid paraffin | 150 g |
| Spermaceti | 50 g |
| Sorbitan monopalmitate | 50 g |
| Polyoxyethylene sorbitan monopalmitate | 50 g |
| Water | 530 g |
| | 1000 g |

Heat petrolatum, paraffin, spermaceti, sorbitan-monopalmitate, and polyoxyethylene sorbitan monopalmitate to 70° C. and add slowly the water at 72° C. with agitation. Continue agitation until the cream has cooled. Triturate 3-deoxy-3β-bromo-16-deacetoxy-16β-acetylthio-24,25-dihydrofusidic acid into the cream base and homogenize using a roller mill. Fill the cream into laquered aluminium collapsible tubes.

EXAMPLE 65

| Ointment | |
|---|---|
| 16-Deacetoxy-16β-benzoylthio-24,25-dihydrofusidic acid potassium salt | 20 g |
| Liquid paraffin | 138 g |

-continued

| Ointment | |
|---|---|
| Cetanol | 4 g |
| Lanolin anhydrous | 46 g |
| Petrolatum | 792 g |
| | 1000 g |

Melt paraffin, cetanol, lanolin, and petrolatum at 70° C. After cooling to below 40° C., triturate 16-deacetoxy-16β-benzoylthio-24,25-dihydrofusidic acid potassium salt. Fill the ointment into laquered collapsible aluminium tubes.

EXAMPLE 66

| Capsule | |
|---|---|
| 16-Deacetoxy-16β-(acetylthio)fusidic acid potassium salt | 250 g |
| Microcrystalline cellulose | 145 g |
| Magnesium stearate | 5 g |
| | 400 g |

Pass the ingredients through a 60 mesh sieve and mix for 10 minutes. Fill the mixture into hard gelatin capsules No. 00 (Parke Davis & Co.) using a capsule fil weight of 400 mg.

EXAMPLE 67

| Tablets | |
|---|---|
| 16-Deacetoxy-16β-acetylthio-24,25-dihydro-fusidic acid potassium salt | 250 g |
| Avicel PH 101 | 120 g |
| STA-Rx 1500 | 120 g |
| Magnesium stearate | 10 g |

16-Deacetoxy-16β-acetylthio-24,25-dihydrofusidic acid potassium salt, Avicel, and STA-Rx are mixed together, sieved through a 0.7 mm sieve and thereafter mixed with the magnesium stearate. The mixture is pressed into tablets each of 500 mg.

EXAMPLE 68

| Preparation of suspension | |
|---|---|
| 16-Deacetoxy-16β-(acetylthio)fusidic acid | 5.00 g |
| Citric acid | 0.45 g |
| Sodium monohydrogenphosphate | 0.70 g |
| Sucrose | 25.00 g |
| Tween 80 | 0.05 g |
| Potassium sorbate | 0.20 g |
| Carboxymethylcellulose-Na | 0.50 g |
| Purified water | qs to 100 ml suspension |

The crystals are micronized and suspended in a solution of the citric acid, the sodium monohydrogenphosphate, the sucrose, the potassium sorbate and the Tween 80 in 50 ml water, if necessary under slight warming. The carboxymethylcellulose-Na is dissolved in 20 ml of boiling water. After cooling, it is added to the other ingredients. The suspension is homogenized in a blender and finally purified water is added to a total volume of 100 ml.

EXAMPLE 69

| Cream | |
|---|---|
| 16-Deacetoxy-16β-(acetylthio)fusidic acid (A) | 10 g |
| 3α,11α-Dihydroxy-16β-isopropylthiofusida- | |

-continued

| Cream | |
|---|---|
| 13(17),24-dien-21-oic acid (B) | 10 g |
| Petrolatum | 150 g |
| Liquid paraffin | 150 g |
| Spermaceti | 50 g |
| Sorbitan monopalmitate | 50 g |
| Polyoxyethylene sorbitan monopalmitate | 50 g |
| Water | 530 g |
| | 1000 g |

Heat petrolatum, paraffin, spermaceti, sorbitan-monopalmitate, and polyoxyethylene sorbitan monopalmitate to 70° C. and add slowly the water at 72° C. with agitation. Continue agitation until the cream has cooled. Triturate A and B into the cream base and homogenize using a roller mill. Fill the cream into laquered aluminium collapsible tubes.

EXAMPLE 70

| Ointment | | |
|---|---|---|
| 16-Deacetoxy-16β-acetylthio-24,25-dihydro-fusidic acid potassium salt (A) | 2.5 | g |
| 3α,11α-dihydroxy-16β-isopropylthio-fusida-13(17),24-dien-21-oic acid potassium salt (B) | 7.5 | g |
| Liquid paraffin | 138 | g |
| Cetanol | 4 | g |
| Lanolin anhydrous | 46 | g |
| Petrolatum | 802 | g |
| | 1000 | g |

Melt paraffin, cetanol, lanolin, and petrolatum at 70° C. After cooling to below 40° C., triturate A and B. Fill the ointment into laquered collapsible tubes.

What we claim is:

1. A compound of the formula I

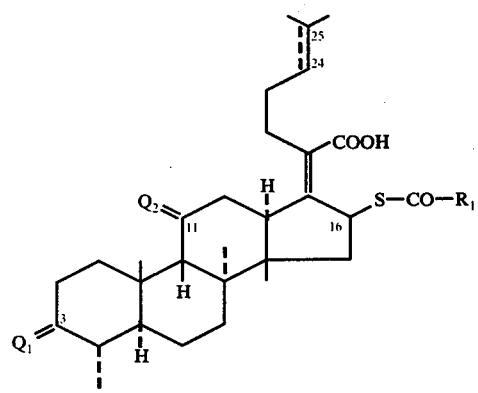

in which the dotted line between C-24 and C-25 indicates that the carbon atoms in question are connected by either a double bond or a single bond and in which $Q_1$ represents oxygen or one of the groupings

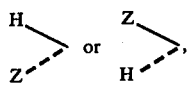

Z being a hydroxy group, a halogen atom, a methylsulfonyloxy or p-tolylsulfonyloxy group, an azido or a nitro group, $Q_2$ is oxygen or the grouping

and $R_1$ stands for a straight or branched alkyl radical having from 1 to 6 carbon atoms, a phenyl or a heterocyclyl radical having 5 or 6 ring atoms and containing nitrogen, oxygen and/or sulfur atoms, these radicals being optionally substituted with, nitro, lower alkyl radicals; or pharmaceutically acceptable, non-toxic salt or easily hydrolyzable ester thereof.

2. A compound according to claim 1, in which $Q_1$ stands for the grouping

Z having the meaning defined in claim 1.

3. A compound according to claim 1, in which $Q_1$ stands for the grouping

Z having the meaning defined in claim 1.

4. A compound according to claim 1, in which $Q_1$ stands for oxygen.

5. A compound according to claim 1, in which $Q_2$ stands for oxygen.

6. A compound according to claim 1, in which $R_1$ stands for methyl.

7. A compound according to claim 1, in which $R_1$ stands for phenyl.

8. A compound according to claim 1, in which the bond between C-24 and C-25 is a double bond.

9. A compound according to claim 1, in which the bond between C-24 and C-25 is a single bond.

10. 16-Deacetoxy-16β-(acetylthio)fusidic acid, or pharmaceutically acceptable, non-toxic salt or easily hydrolyzable ester thereof.

11. 16-Deacetoxy-16β-acetylthio-24,25-dihydrofusidic acid, or pharmaceutically acceptable, non-toxic salt or easily hydrolyzable ester thereof.

12. 11-Keto-16-deacetoxy-16β-(acetylthio)fusidic acid, or pharmaceutically acceptable, non-toxic salt or easily hydrolyzable ester thereof.

13. 16-Deacetoxy-16β-benzoylthio-24,25-dihydrofusidic acid, or pharmaceutically acceptable, non-toxic salt or easily hydrolyzable ester thereof.

14. 3-Deoxy-3β-bromo-16-deacetoxy-16β-acetylthio-24,25-dihydrofusidic acid, or pharmaceutically acceptable, non-toxic salt or easily hydrolyzable ester thereof.

15. A pharmaceutical preparation in dosage unit form for the enteral or parenteral treatment of patients suffering from infectious diseases, which comprises as an active ingredient at least one compound according to claim 1, or a pharmaceutically acceptable, non-toxic salt or an easily hydrolysable ester thereof, and an atoxic pharmaceutically acceptable carrier, the quantity of the said active compound being between 0.05 g and 1 g.

16. A preparation as claimed in claim 15 wherein the dosage unit contains from 0.2 g to 0.75 g of at least one active compound.

17. A preparation as claimed in claim 15 wherein the dosage unit is in the form of a tablet.

18. A preparation as claimed in claim 15 wherein the dosage unit is in the form of a capsule.

19. A parenteral pharmaceutical preparation in dosage unit form, containing from 0.05 g to 1 g of at least one compound according to claim 1 or a salt or ester thereof as defined in claim 1 as dry matter, in an ampoule, vial or other suitable receptacle, for reconstitution.

20. A preparation according to claim 15, dissolved or suspended in a non-toxic, pharmaceutically acceptable vehicle.

21. A pharmaceutical preparation for oral treatment in form of a sustained-release preparation in dosage unit form of at least one compound of claim 1, in which the dose of the active compound is between 0.05 g to 1 g.

22. A preparation for oral treatment in the form of a suspension of at least one compound according to claim 1 as such or of a sparingly soluble salt or ester thereof, said preparation containing from 20 to 250 mg per ml of a non-aqueous vehicle.

23. A preparation for topical treatment in the form of a powder or an ointment or cream containing at least one compound of formula I or a salt or ester as defined in claim 1 in an amount of from 0.5 g to 10 g per 100 g of the preparation.

24. A preparation as claimed in claim 15 in which the dosage unit additionally contains other antibiotics.

25. A preparation according to claim 24 which in addition contains a penicillanic acid antibiotic.

26. A preparation according to claim 24 which in addition contains a cephalosporanic acid antibiotic.

27. A preparation according to claim 24 which in addition contains a fusidic acid antibiotic.

28. A preparation according to claim 24 which in addition contains a tetracycline antibiotic.

29. A method of treating patients suffering from infectious bacterial diseases, comprising administering to (adult) patients from 0.25 to 4 g per day of at least one compound of formula I of claim 1 or an equivalent amount of a salt or ester thereof as defined in claim 1.

30. A method according to claim 29, in which a preparation according to claim 19 is used.

* * * * *

UNITED STATES PATENT AND TRADEMARK OFFICE
CERTIFICATE OF CORRECTION

PATENT NO. : 4,119,717
DATED : October 10, 1978
INVENTOR(S) : Welf von Daehne and Poul Rodbroe Rasmussen It is certified that error appears in the above-identified patent and that said Letters Patent are hereby corrected as shown below:

Item [75] after "Rodbroe" delete the comma ","

Column 9, after the formula in Table I and before "$Q_1$" change "Example" to --Preparation--

Column 19, in the formula, Table VII, "O-CO-$CH_3$" should read --S-CO-$CH_3$--

Column 24, the formula in Table X should read:

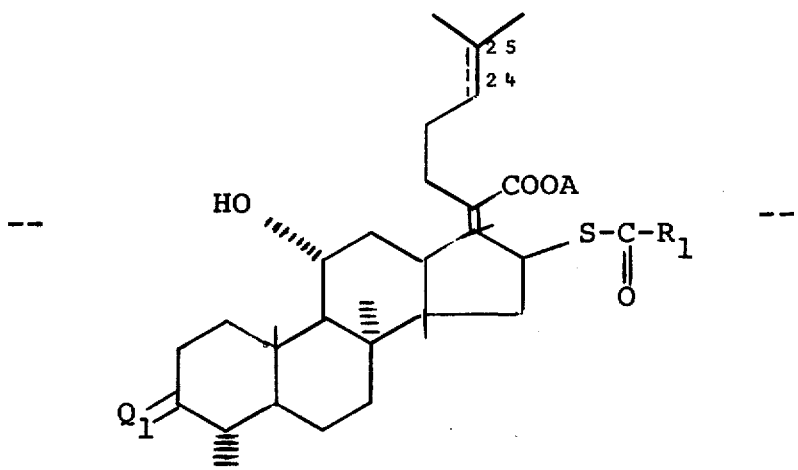

UNITED STATES PATENT AND TRADEMARK OFFICE
CERTIFICATE OF CORRECTION

PATENT NO. : 4,119,717

DATED : October 10, 1978

INVENTOR(S) : Welf von Daehne and Poul Rodbroe Rasmussen

It is certified that error appears in the above-identified patent and that said Letters Patent are hereby corrected as shown below:

Column 25, the formula Table X should read:

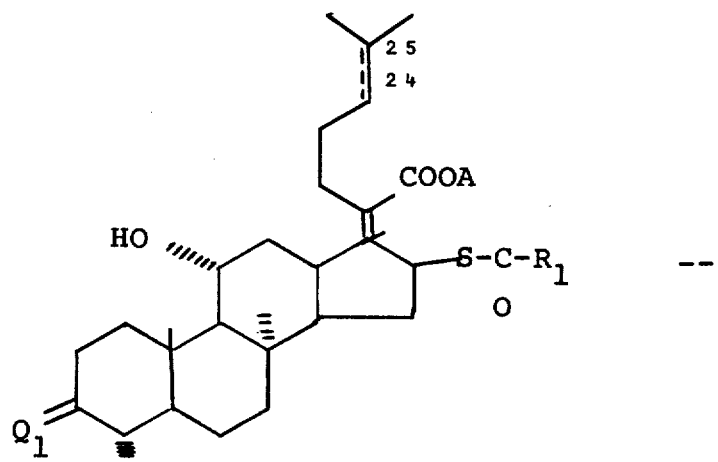

Signed and Sealed this

Fourth Day of March 1980

[SEAL]

Attest:

SIDNEY A. DIAMOND

Attesting Officer

Commissioner of Patents and Trademarks